United States Patent [19]

Sovak et al.

[11] Patent Number: 5,741,924
[45] Date of Patent: Apr. 21, 1998

[54] SUNBLOCKING POLYMERS AND THEIR FORMULATION

[75] Inventors: Milos Sovak, La Jolla; Ronald Calvin Terry; James Gordon Douglass, III, both of San Diego; Farid Bakir, Del Mar, all of Calif.

[73] Assignee: Biophysica Inc., La Jolla, Calif.

[21] Appl. No.: 490,316

[22] Filed: Jun. 14, 1995

Related U.S. Application Data

[63] Continuation-in-part of Ser. No. 164,881, Dec. 9, 1993, Pat. No. 5,487,885, which is a continuation-in-part of Ser. No. 994,426, Dec. 21, 1992, abandoned.

[51] Int. Cl.$^6$ .................... C07C 229/00; C07C 49/36; A61K 7/42
[52] U.S. Cl. .................. 560/43; 568/337; 424/59
[58] Field of Search ............. 560/55, 43; 564/170, 564/171, 174, 157; 424/59, 60; 568/337

[56] References Cited

U.S. PATENT DOCUMENTS

| | | | |
|---|---|---|---|
| 2,764,613 | 9/1956 | Grunwald | 564/171 |
| 3,980,617 | 9/1976 | Jacquet et al. | 424/59 |
| 4,003,990 | 1/1977 | Jacquet et al. | |
| 4,233,430 | 11/1980 | Jacquet et al. | |
| 4,525,061 | 6/1985 | Cho et al. | |
| 4,661,616 | 4/1987 | Hill | 560/55 |
| 5,041,282 | 8/1991 | Sabatelli et al. | |
| 5,063,048 | 11/1991 | Saitoh et al. | |
| 5,134,223 | 7/1992 | Langer et al. | |
| 5,243,021 | 9/1993 | Langer et al. | |
| 5,250,652 | 10/1993 | Langer et al. | |
| 5,487,885 | 1/1996 | Sovak et al. | 424/59 |

FOREIGN PATENT DOCUMENTS

| | | | |
|---|---|---|---|
| 888664 | 1/1962 | United Kingdom | 564/194 |
| WO 93/22413 | 11/1993 | WIPO | |

OTHER PUBLICATIONS

C.A. 113: 84646 Shairishi et al 1990/C.A. 111:140208 Ker et al '89.
C.A. 91: 145926 Tirrell et al 1979.
C.A. 113; 217980 Shah et al 1990.
C.A. 68: 3801 Japanese Geon Ltd. 1968.
Dromgoole, et al., "Sunscreening Agent Intolerance, Contact and Photocontact Sensitization and Contact Urticaria", J. Amer. Derm. (1990), 22:1068–1078.
Lowe, Photoprotection. Sem Derm. (1990), 9:78–83.

*Primary Examiner*—Peter F. Kulkosky
*Attorney, Agent, or Firm*—Richard F. Trecartin; Flehr Hohbach Test Albritton & Herbert LLP

[57] ABSTRACT

Novel polymeric compositions and their intermediates are provided, providing for broad range protection from ultraviolet radiation. Acryl polymers comprising at least two different ultraviolet absorbing moieties having different light absorbing ranges are employed in conjunction with another hydrophilic monomer to provide sunscreen formulations for invisibility, and enhanced protection, without deleterious effects in the dermis.

3 Claims, No Drawings

SUNBLOCKING POLYMERS AND THEIR FORMULATION

CROSS-REFERENCE TO RELATED APPLICATIONS

This application is a continuation-in-part of application Ser. No. 08/164,881, now U.S. Pat. No. 5,487,885 which is a continuation-in-part of application Ser. No. 07/994,426, filed Dec. 21, 1992, now abandoned.

INTRODUCTION

1. Technical Field

The field of this invention is sunblock compositions for use in dermatological and ophthalmological applications.

2. Background

The role of ultraviolet radiation and skin aging in development of skin cancer, as well as eye cataracts, is being increasingly recognized. For the protection of the skin, the state of art utilizes various UV-absorbing compounds, primarily singular (monomeric) aromatic compounds and/or reflecting pigments, i.e. metal oxides., formulated into creams and lotions. Intraocular and contact soft lenses are described with such compounds added into the hydrogel, or coating the lens surfaces with UV-absorbing preparations. Ophthalmologic solutions are described which claim protection against UV radiation using various compounds added to standard eyedrop formulations.

There are many disadvantages to the known UV blockers. One is their lack of biological tolerance. Due to their toxicity and allergenicity, as well as other side-effects, the various UV-absorbing additives, in spite of being strictly limited and regulated, often exercise their toxicity potential. Also, as these UV-blocking compounds penetrate into the skin, they convert the absorbed UV radiation into heat, which in turn dilates the vessels which is perceived as unpleasant.

The reflecting inorganic pigments, such as zinc or titanium oxides, are visible on the skin, even if micronized and/or tinted.

For ophthalmic use, the protection afforded by the ophthalmic solutions containing the toxic monomers is inefficient. The concentration limitation imposed by the toxicity of the compounds prevents formulations providing adequate protection. In hydrogel lenses, the monomers leak out. Coating such lenses in a permanent way is, on the other hand, difficult and costly.

An ideal sun radiation blocking agent should be non-toxic, should be invisible on the surface of the skin or eye, and non-absorbable to be biologically inert. The blocking agent should cover the entire UV range of atmospheric radiation. Desirably, the blocking agent should absorb, reflect or at least diffract the infrared radiation known to potentiate the carcinogenic and inflammatory effect of the ultraviolet light. There is, therefore, substantial interest in developing sun blocking agents which approximate this ideal.

Relevant Literature

Dromgoole and Maibach, *J. Am. Academy of Dermatology*, Mosby Year Book, 1990, Chapter 8, describe contact sensitization and photocontact sensitization of sunscreening agents. Harber, et al., in *Photosensitivity Diseases, Principles of Diagnosis and Treatment*, B. Decker, Toronto, 1989, Chapter 10, page 141, describe intrinsic and extrinsic photoprotection against UV-B and UV-A radiation. Lowe, ibid., Chapter 11, page 161 describes the screening of various sun protection compositions.

In Japanese application No. 5-125118, filed Nov. 2, 1991, a para-amino benzoyl substituted polyacrylic acid as a sun blocking composition is reported, where a para-aminobenzoyl group is joined to the polyacrylic acid by a variety of linking groups. See also CA102:221311d which describes para-aminobenzoyl substituted acrylic polymers.

SUMMARY OF THE INVENTION

UV absorbing acrylic polymers are provided having a plurality of UV absorbing moieties which substantially cover the wave-length range of light (sunlight) which penetrates to the earth's surface. The polymers will include an additional monomer to render the polymer, in a given solvent, invisible, and they may include a cross-linker. The polymers may be formulated in conventional ways for invisibility and stability. The formulations provide for protection against deleterious effects of UV radiation on the skin and eyes. The compositions may also find use in opthamalogical applications.

DESCRIPTION OF SPECIFIC EMBODIMENTS

Novel sun blocking polymeric compositions are provided comprising at least two different UV absorbing moieties and a moiety containing different substituents on the acrylic backbone. The compositions find use as sun blocking agents in a variety of contexts. The polymers may be prepared by combining the individual monomers under addition polymerizing conditions or precipitation or emulsification in appropriate amounts, taking into consideration the differential rates of incorporation of the different monomers, whereby a product is obtained having an effective proportion of monomers which absorb UV light in the wave length range to which skin is normally exposed on earth.

Normally, UV absorbers of at least UV-A and UV-B will be present, and there could be an absorber for UV-C. In addition, there will be at least one other monomer which will have a hydrophobic or hydrophilic substituent on the acryl group, the latter having one or more hydroxy groups. For the most part, the number ratio of total UV absorbers to other monomer(s) in the polymer will be in the range of about 0.1–10:1, usually 0.5–5:1, more usually 1–5:1. Of the UV absorbers present, there will generally be about 30–98 number percent of the UV-B absorber, more usually from about 50 to 95 number %, at least 2 number percent of the UV-A absorber, usually at least about 5 number %, and the remainder being the UV-C absorber. Depending upon the individual monomers, the ratio of the UV absorbing monomers to the other monomers in the polymerization reaction mixture, the absence or presence of a cross-linking agent, and the like, the molecular weight may vary widely, where the composition of individual molecules may vary as the polymerization proceeds. To obtain high molecular weight polymer, it will be desirable to use small amounts of a cross-linking agent, generally from about 0.5–10 mole percent, more usually from about 1–3 mole percent of total monomer.

For eye lens applications, the polymeric composition will be insoluble in water, but desirably will swell in the aqueous media formulation. This can be readily achieved by appropriate ratios of the hydrophilic monomer to the UV absorbing monomers and the number of hydrophilic groups associated with the hydrophilic monomer and appropriate use of the crosslinker.

In addition, the UV monomers should have high extinction coefficients, at least about 20,000, preferably in excess of about 25,000.

The UV-A absorbers will, for the most part, be benzophenones or bis-benzoylmethane compounds, substituted with appropriate substituents for providing the desired light absorption characteristics, as well as for linking to the acryl group. For the most part, the UV-A absorbers of the subject composition will have the following formula:

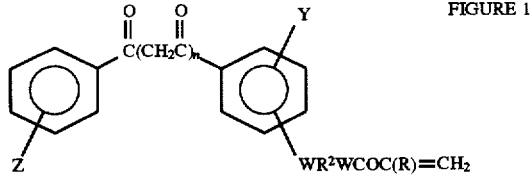

FIGURE 1 wherein:

n is 0–1;

R is H, alkyl of from 1 to 3, usually 1 to 2, carbon atoms, which may be substituted with a functional group having from 1 to 2 heteroatoms, which are N or O;

$R^2$ is a divalent hydrocarbylene group or substituted hydrocarbylene group, having up to 2, usually up to 1 substituent, where the substituent will be composed of oxygen, nitrogen, phosphorus, carbon and hydrogen, having from 1 to 3 heteroatoms, usually 1 to 2 heteroatoms, where the heteroatom may be in the chain, and from 0 to 6, usually 0 to 4 carbon atoms, which group may be aliphatic, alicyclic or aromatic, generally of from 2–8, more usually of from 2–6 carbon atoms, particularly phenylene or alkylene;

Z is oxy, particularly hydroxy or alkoxy of from 1–6, more usually 1–3 carbon atoms, or amino having from 0–2 alkyl substituents having a total of from about 1–12, more usually from about 1–6 carbon atoms, or hydrogen;

Z will preferably be at the para position to the carbonyl group;

Y is non-oxo carbonyl, which includes the carboxylic acid, carboxyl ester, where the ester will normally have an alkyl group of from 1–6, usually from 1–3 carbon atoms, or carboxamide, where the amino may be substituted or unsubstituted, where the substituted amino will have from 1–2 alkyl substituents with a total of from 1–12 carbon atoms, usually of from 1–6 carbon atoms;

Y is preferably at the ortho position in relation to the carbonyl;

W is oxy (—O—) or amino (—N($R^1$)), where $R^1$ is hydrogen or alkyl of from 1–6, usually 1–3 carbon atoms, where W is preferably oxy, when n is 1;

W is preferably substituted at the para position to the carbonyl;

there being from 0–2, usually 0–1 Y.

In addition, the rings may be substituted with from 0–3, usually 0–2 alkyl groups of from 1–6, more usually 1–3 carbon atoms, at available positions on the rings.

For the UV-B absorbers, the compounds for the most part will be benzoyloxy derivatives, particularly substituted benzoyloxy derivatives, more particularly para-amino substituted benzoyloxy derivatives. For the most part, these compounds will come within the following formula:

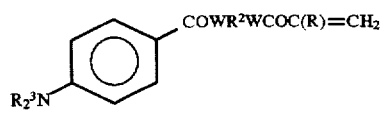

FIGURE 2 wherein:

$R^3$ is hydrogen or alkyl of from 1–6, usually 1–3 carbon atoms, preferably methyl;

and

W, R and $R^2$ are as defined previously.

The UV-C absorbing compound will be an oxybenzoyl derivative bonded to an acryl group through a divalent bridging moiety. For the most part, the UV-C absorbing group will have the following formula:

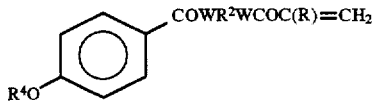

FIGURE 3 wherein:

$R^4$ is hydrogen or alkyl of from 1–6, usually 1–3 carbon atoms, preferably methyl, and the remaining symbols have been defined previously.

The remaining monomers may be substituted or unsubstituted will usually have at least one organic substituent, which may be the same or different as to the individual monomers, there usually being a total of not more than about 4 different groups, the substituent being unsubstituted or more usually having at least one polar group, particularly an oxy group on a side chain. For the most part, these compounds will be of relatively low molecular weight, generally being under about 800 Dal, more usually being under about 400 Dal. They will normally be aliphatic, particularly saturated aliphatic, i.e. alkyl, of from 1 to 6, usually 2 to 6 carbon atoms, have at least 1 oxy group and may have up to 4 oxy groups, generally having from 1–3 oxy groups, more usually having from 1–3 hydroxy groups. For the most part, these compounds will have the following formula:

$R^5WCOC(R)=CH_2$  FIGURE 4 wherein:

$R^5$ is hydrogen, a counterion, e.g. alkali metal, ammonium, etc., an aliphatic group of from 1–8 carbon atoms, usually 1–6 carbon atoms, particularly alkyl, having from 1–5, usually 1–3 oxy groups, more usually hydroxy groups;

the remaining symbols have been defined previously.

Monomers of interest are acrylic acid, methacrylic acid, and their hydrophilic and hydrophobic amides or esters, such as hydroxyethyl and hydroxypropyl amides and esters, and ethyl, propyl, butyl, pentyl and hexyl amides and esters.

In the above formulas, the oxy or amino substituent may be substituted with a 2-nitrovinyl group to provide the desired radiation absorbing characteristics.

Compounds of interest include building blocks of p-aminobenzoic acid, p-methoxybenzoic acid, o-hydroxybenzoyl, p-dimethylaminobenzoic acid, p-aminobenzoyl, acetoxyhydroquinone, phenylenediamine, etc.

Compounds of interest include N,N-dialkylamino, N'-acryl or methacryl phenylenediamine, p-acryloxy or methacryloxybenzoate alkyl ester, N-alkyl m-acrylamido- or methacrylamidobenzoatealkyl ester, p-benzoyloxyacrylanilide or -methacrylanilide, p-acrylamido or -methacrylamidobenzoate methyl ester, o-acryloxy or -methacryloxy-dibenzoylmethane, p-acryloxy or -methacrylamidodibenzoylmethane, 4-acetoxy-1-acryloxy or -methacryloxybenzene, 2,4-dimethylamino-1-acryloxy or -methacryloxybenzene, N,N-bis-(3-acryloxy or -methacryloxyphenyl) methylamine, m-acryloxy or -methacryloxy-dibenzoylmethane, p,p'-diacryloxy or -methacryloxydibenzoylmethane, m,m'-diacryloxy or -methacryloxydibenzoylmethane, m,p'-diacryloxy or -methacryloxydibenzoylmethane, m- or p-acryloxy or -methacryloxy-2-nitrostyrene, 4-acryloxy or -methacryloxy-4,-(1"-(2"-nitrovinyl))dibenzoyl-methane, and the like, where alkyl is 1–3, usually 1 carbon atom.

Any convenient cross-linking agent may be employed, which will usually be a bis-acryl or -methacryl, where the linking group may be any convenient group. Thus, the linking group may be methylene, amino, particularly substituted amino, 1,2-dioxyethylene, oxyamino, diaminoethylene, 1,4-dioxybutylene, dialkylenephosphate ester, α,α'-xylylenediamino, etc.

Polymers of particular interest comprise from about 20 to 60, usually 25 to 60 mol % acrylic acid. In addition, the mol ratio of the UV-B to UV-A monomers will generally be in the range of 75:25 to 98:2, preferably 85:15 to 95:5. Of interest is to use a p-aminobenzoic acid derivative as the UV-B moiety. Polymers coming within this composition tend to readily form small particles without grinding, where the particles may be directly used in the sunscreen formulation.

The subject monomers may be prepared from commercially available intermediates in accordance with known ways. A substantial number of starting monomers are provided in the accompanying working exemplification, which may serve as models for the production of a variety of monomers coming within the subject invention. In addition, the polymerization may be carried out in accordance with conventional ways, using free radical catalysts at relatively mild temperatures and a solvent system to achieve emulsion or suspension in situ. Thus, peroxy compounds, azo compounds, ultraviolet light, or the like may be used as a source of polymerization initiation at temperatures in the range of about 10°–70° C. for the polymerization. Usually, the polymerization will take place in the absence of oxygen, preferably under an inert atmosphere. The time for the polymerization will usually be at least an hour, usually at least 2 hours, and may extend to 24 hours or more, depending upon the conditions for the polymerization. A solvent may be used, e.g. an alkanol, particularly methanol, or a hydrocarbon, such as toluene, or the like, in which the various monomers are soluble. Generally, the solvent may be present in from about 0.2–10:1 weight ratio to the monomer charge. In the preparation of hydrophobic particulate polymers, the acrylic acid derivative may serve as a solvent, and an inhomogeneous system containing water may be employed After completion of the polymerization, the polymer may be isolated in accordance with conventional ways, and purified as appropriate.

The subject polymers may be readily formulated with appropriate vehicles to provide the desired composition. For dermatological use, the subject polymers may be formulated in creams, lotions, salves, and the like, to produce an adherent smooth invisible film and to partially diffract the UV and infrared radiation. A wide variety of emollients are taught in the literature and include polyethylene glycols, polypropylene glycols, silicone, mineral vegetable oils, petrolatum (purified petroleum hydrocarbon greases), and the like. Depending upon the nature of the polymeric product, the polymeric product may be milled, ground or otherwise reduced in particle size in the presence of an oil, conveniently a hydrocarbon oil. Of interest is the use of additives, such as other microparticles of other polymers, such as partially hydrolyzed polyacrylamides or ultrafine titanium or zinc oxides, although the latter do not absorb but only partially diffract or reflect UV light. Where other microparticles are added, the mixture may be further ground to provide a uniform mixture of microparticles.

For the preparation of UV-absorbing eye lenses, the appropriate composition of monomers is polymerized in lens forms or molds.

The polymers of the subject invention will be present in the formulation in at least about 5 weight percent and not more than about 70 weight percent, usually ranging from about 10–40 weight percent. The dermatological formulation may be coated, sprayed, spread or otherwise applied to the particular surface, e.g., skin, as required and will be retained at the surface for extended periods of time.

The following examples are offered by way of illustration and not by way of limitation.

EXPERIMENTAL

Example 1: Synthesis of an Acrylamide Derivative of an Carboxy-Substituted Benzophenone 40 g (210 mmol) of 2-aminobenzophenone-2'-carboxylic acid were placed in a L reaction flask followed by 500 ml of EtOH and 111 ml of 9.5 N NaOH (1.05 moles). 100 ml of $H_2O$ were added to dissolve sodium salts. With stirring and cooling to 0°–5° C., 4.0 eq of acryloyl chloride were added over 10 minutes. The reaction was monitored by reverse phase HPLC. After completion, EtOH was removed by evaporation, and the reaction mixture acidified with HCl. A solid precipitated and was filtered. The yield of 2-acrylaminobenzophenone-2'-carboxylic acid was 53 g (86%).

Example 2: Acylation of 4-Amino Benzophenone with Acryloyl Chloride

4-Aminobenzophenone (10 g, 51 mmol, 1.00 eq) was dissolved in 40 ml of THF. After cooling to 5° C., acryloyl chloride (4.62 g, 51 mmol, 1.00 eq, in 10 ml THF) was added followed by triethylamine to scavenge the generated HCl.

THF was removed by rotary evaporation, the resulting oil was dissolved in 100 ml of ethyl acetate and the organic solution extracted with 3×50 ml of $H_2O$. Ethyl acetate was removed by rotary evaporation and the product was collected as a solid in a yield of 10.5 g (82%).

Example 3: N-acylation of p-hydroxyaniline with p-anisoyl chloride p-Hydroxy aniline (152.6 g, 1.398 moles) was dissolved in 1.9 L tetrahydrofuran and 113 ml (110.6 g, 1.398 moles) pyridine. p-Anisoyl chloride (238.5 g, 1.398 moles) was added dropwise at 20° C. over 2.5 hours. After stirring an additional 2 hours at 20° C., the solid was filtered and washed with tetrahydrofuran. The product, 466.5 g after drying, was refluxed in 3 L methanol for 1.5 hours, then cooled, filtered and washed with methanol. After vacuum drying, the solid weighed 262.8 g, yield 77%.

Example 4: Acylation of 4-methoxy-N-[1-(4-hydroxyphenyl)] benzamide with methacryloyl chloride 4-Methoxy-N-[1-(4-hydroxyphenyl)] benzamide (200 g, 0.8221 moles) was dissolved in 650 ml dimethylacetamide and triethylamine (91.52 g, 0.9043 moles) and then cooled to −15° C. Methacryloyl chloride (94.53 g, 0.9043 moles) was added dropwise over an hour at −10° C., the suspension was suspension. After warming to 20°–25° C., the suspension was diluted with 650 ml acetonitrile. The resulting solid was filtered, washed with acetonitrile and vacuum dried to 300 g and then refluxed in 1.5 L methanol for 1.5 hours. After cooling to 20°–25° C., the suspension was filtered, washed with methanol, and vacuum dried to 177 g of product, yield 69%.

Example 5: Acylation of 4-aminobenzoic acid with acryloyl chloride

4-Aminobenzoic acid (10.00 g, 0.073 moles) was dissolved in a mixture of water (20 ml), ethanol (50 ml) and 5 N NaOH (37 ml). After cooling to 10° C., acryloyl chloride (8.58 g, 0.095 moles) was quickly added with stirring. Additional 1 N NaOH (125 ml) and acryloyl chloride (8.58 g, 0.095 moles) were added to push the reaction to completion. The reaction was acidified to pH 1 with 6 N HCl (25 ml) to produce a suspension that was filtered, washed with water and dried to a solid. Resuspension of the solid in acetonitrile (200 ml) at 60° C., followed by filtration, led to a solid product that weighed 10.1 g (Yield 72%) after vacuum drying.

Example 6: Amidation of 4-acrylamidobenzoic acid with aniline

4-Acrylamidobenzoic acid (1.912 g, 10 mmol) was dissolved in 10 ml chloroform and triethylamine (1.113 g, 11 mmol). After cooling to −25° C., chloroethylformate (1.193 g, 11 mmoles) in 3 ml chloroform was added dropwise with stirring. After 2 hours at −25° C., aniline (0.931 g, 10 mmoles) in 2 ml acetonitrile was added dropwise with stirring. The reaction was slowly warmed to 20° C., stirred for 16 hours, filtered, washed with chloroform, and dried to a mass of 1.46 g. This solid was dissolved in a mixture of ethyl acetate and isopentyl alcohol, and extracted twice with a bicarbonate solution. The organic layer was separated, dried over $MgSO_4$, filtered, and evaporated to dryness to give 1.30 g (50% yield).

Example 7: Amidation of 4-dimethylaminobenzoyl chloride with ethanolamine

4-Dimethylaminobenzoyl chloride (1.24 g, 6.75 mmoles) was dissolved in 15 ml tetrahydrofuran and then added dropwise to a stirred solution of ethanolamine (0.865 g, 14.17 mmoles) in 6 ml tetrahydrofuran held at −5° C. After the 20 minute addition, the reaction was slowly warmed to 20°–25° C. Tetrahydrofuran was removed in vacuo and the solids were stirred with 15 ml water for 25 minutes. The resulting product was filtered, washed with water and vacuum dried to 1.13 g. This solid was crystallized from N-propanol yielding 0.92 g (65%) of the desired product.

Example 8: Chlorination of 4-dimethylaminobenzoic acid

4-Dimethylaminobenzoic acid (250 g, 1.51 moles) was suspended in 2 L of ethyl acetate. Thionyl chloride (359.3 g, 3.02 moles) was added dropwise with stirring. After completion of the reaction, the solvent was removed by rotary evaporation affording a gray solid. The solid was crystallized from ethyl acetate to give 216 g of 4-dimethylaminobenzoyl chloride, yield 78%.

Example 9: Acylation of 2-hydroxyethyl methacrylate with 4-dimethylaminobenzoyl chloride 4-Dimethylaminobenzoyl chloride (216 g, 1.18 moles) was suspended in 500 ml of ethyl acetate. 2-Hydroxyethyl methacrylate (169 g, 1.30 moles) was dissolved in 500 ml ethyl acetate and 165 ml triethylamine (119 g, 1.18 moles) and was added to the acid chloride with stirring. After completion of the reaction, the product was dissolved in ethyl acetate and extracted with dilute sodium bicarbonate. Ethyl acetate was removed by rotary evaporation and the crude product was crystallized from ethanol to give 188.9 g, yield 58%.

Example 10: Esterification of 4-hydroxydibenzoyl methane with methacryloyl chloride 4-Hydroxydibenzoyl methane (1.97 g, 8.2 mmol) was dissolved in 15 ml of ethyl acetate and 1.25 ml of triethylamine (0.91 g, 8.98 mmol). Methacryloyl chloride (0.98 g, 9.4 mmol) was dissolved in 5 ml of ethyl acetate and added dropwise with stirring. Triethylamine hydrochloride was removed by extraction and ethyl acetate was removed by rotary evaporation. Crystallization from ethanol yielded 1.65 g of product, yield 65%.

Example 11: 4-Tetrahydropyranyloxyacetophenone

4-Hydroxyacetophenone (75.00 g, 0.55 mol) was dissolved in ethyl acetate (300 ml) and a catalytic amount of methanesulfonic acid. The solution was cooled to 0°–4° C. Dihydropyran (204 ml, 2.20 moles, 4.0 eq) was slowly added. At the end of the addition, the ice-water bath was removed and the reaction was allowed to proceed at room temperature. A few minutes later a heavy white precipitate was formed and the slurry was transferred into a separatory funnel where it was washed with water. The organic layer was dried over anhydrous sodium sulfate. Removal of the solvent under reduced pressure afforded a white fluffy solid. The solid was recrystallized from hexane. The yield was quantitative.

Example 12: 4-Hydroxydibenzoyl methane

4-Tetrahydropyranloxyacetophenone (0.50 g, 2.11 mol) was dissolved in freshly distilled THF (6.0 ml). Sodium hydride (60% suspended in mineral oil, 170 mg, 4.23 mmol) was added. The mixture was stirred at room temperature and methyl benzoate (0.53 ml, 4.23 mmol) was added. The mixture was stirred at room temperature for an additional three hours. The reaction was quenched with the addition of methanol. After solvent removal, the crude oil was dissolved in methylene chloride and washed with a 0.02 N aqueous solution of oxalic acid. The organic layer was then dried over anhydrous sodium sulfate. The crude product was dissolved in methanol (30 ml) and a 2 N aqueous solution of oxalic acid (10 ml) was added. The solution was stirred for 2 hours at 42° C. The solvent was partially removed with the Rotavapor and a yellow solid was recovered upon filtration. The solid was dissolved in a minimum of hot ethanol and was precipitated by addition of hexane. A yellow solid (0.456 g, 1.90 mmol, 90%) was isolated.

Example 13: Acylation of 4-hydroxydibenzoylmethane with acryloyl chloride

4-Hydroxydibenzoyl methane (10.00 g, 41.62 mmol) was dissolved in freshly distilled THF (25.0 ml). The solution was cooled to 0° C. and diazobicycloundecene (DBU) (7.50 ml, 50.00 mmol) was slowly added at 0° C. Acryloyl chloride (5.92 ml, 72.84 mmol) was then added slowly at 0° C. After one hour stirring, the reaction was quenched by addition of methanol. Solvent removal afforded an oil. The crude oil was dissolved in a dichloromethane/hexane mixture. Purification was carried out by flash chromatography on silica gel utilizing hexane/dichloromethane as eluent. After pooling all relevant fractions and removing the solvent, a clear solid (5.60 g, 46%) was obtained.

Example 14: Acylation of p-hydroxymethacrylanilide with p-anisoyl chloride p-Hydroxymethacrylanilide (20.0 g, 113 mmol) was suspended in 250 ml ethyl acetate and 17.3 ml (12.6 g, 125 mmol) triethylamine. p-Anisoyl chloride (19.26 g, 113 mmol) was added dropwise at 25° C. over 15 minutes. The reaction was allowed to proceed for 24 hours with stirring at room temperature. The solid was filtered, washed with water (100 ml×3), and then washed with saturated bicarbonate solution (100 ml×3). The solid crystallized from methanol weighed 27.1 g, yield 77%.

Example 15: Acylation of 2-hydroxyethyl methacrylate with p-anisoyl chloride

2-Hydroxyethyl methacrylate (5.00 g, 38.5 mmol) was dissolved in 25.0 ml ethyl acetate and triethylamine (4.25 g, 42.0 mmol). p-Anisoyl chloride (6.48 g, 38.5 mmol) was added dropwise at 5° C. over ten minutes. After addition, the reaction was allowed to reach room temperature and stir for 24 hours. The triethylamine hydrochloride was filtered off and the filtrate washed with water (3×25.0 ml) and saturated bicarbonate solution (3×25.0 ml). The ethyl acetate layer was dried over $MgSO_4$, then stripped to a light yellow oil. The oil was distilled at 200° C. (0.1 mmHg) to yield the desired product.

Example 16: Acylation of N-2-hydroxyethyl acrylamide with p-anisoyl chloride

N-2-hydroxyethyl acrylamide (5.00 g, 43.4 mmol) was dissolved in 35.0 ml ethyl acetate and triethylamine (4.83 g, 47.7 mmol). p-Anisoyl chloride (7.40 g, 43.4 mmol) was added dropwise at 5° C. over ten minutes. After addition, the reaction was stirred for 24 hours at room temperature. The solid was filtered and washed with water (3×25 ml), to remove triethylamine hydrochloride, followed by saturated bicarbonate solution (3×25 ml), and then dried (6.43 g). The initial ethyl acetate filtrate was washed with water (3×25 ml) and saturated bicarbonate solution (3×25 ml). Concentration of the ethyl acetate layer gave two further crops of crystals. Total yield of the three crops: 9.36 g, 93.6%.

Example 17: Acylation of N-[2-hydroxypropyl] methacrylamide with 4-dimethylaminobenzoyl chloride 4-Dimethylaminobenzoyl chloride (56.21 g, 0.306 mol) was combined with N-[2-hydroxypropyl] methacrylamide (42.96 g, 0.30 mol) and 250 ml acetonitrile. The mixture was stirred at room temperature and a solution was briefly obtained before the desired HCl salt of the product crystallized. After filtration, washing with cold acetonitrile and drying, 81.93 g (83.5% yield) of product was obtained.

80.00 g (0.2447 mol) of the HCl salt was suspended in 400 ml dichloromethane while a solution of sodium bicarbonate (21.00 g, 0.25 mol) in 300 ml water was added dropwise. The two phases were filtered to remove turbidity and then separated. The $CH_2Cl_2$ layer was dried on $MgSO_4$, filtered, and evaporated to an oil that was crystallized from ethyl acetate to give 48 g of the free base of the product.

Example 18: Polymerization of a UV-A monomer, a UV-B monomer, and a UV-C monomer A 10 ml vial was charged with 4-methoxy-N-[1-(4-methacryloxyphenyl)] benzamide (156 mg, 0.5 mmol); 4-(dimethylamino) benzoyloxyethyl acrylate (138 mg, 0.5 mmol); 4-acryloxydibenzoyl methane (148 mg, 0.5 mmol); 2-hydroxyethyl methacrylate (98 mg, 0.75 mmol); N,N-methylene bis acrylamide (10 mg, 0.067 mmol); 2,2'-azobisbutyronitrile (3.7 mg, 0.022 mmol); and 3.5 ml methanol. The vial was flushed with argon, sealed and warmed to 60° C. for 20 hours with stirring. The resulting polymeric precipitate was filtered off, washed with methanol, dried to a mass of 0.50 g, and then ground to a fine light yellow powder.

Example 19: Polymerization of a UV-A monomer, a UV-B monomer, and a UV-C monomer A 1 liter flask was charged with 30.83 g (0.1 moles) UV-A monomer 4-methacryloxydibenzoyl methane, 29.04 g (0.1 moles) UV-B monomer N-[2-(4'-dimethylaminobenzoyl) oxypropyl] methacrylamide, 31.13 g (0.1 moles) UV-C monomer 4-methoxy-N-[1-(4-methacryloxyphenyl)] benzamide, 9.76 g (0.075 moles) 2-hydroxyethylmethacrylate, 1.73 g (0.01125 moles) N,N-methylene bisacrylamide, and 500 ml methanol. After flushing with argon, 0.951 g (0.00579 moles) of 2,2-azobis butyronitrile was added along with 250 ml of MeOH. After stirring at 60° C. for 20 hours the sunscreen polymer was filtered, washed with methanol, and vacuum dried to a mass of 90.66 g.

Example 20: Formulation of a Polymeric Sunscreen 2.5 g of the polymeric sunscreen described in Example 19 was mixed with 3 g of petroleum vaseline to produce a fine emulsion with the consistency of a spreadable paste. Upon skin application, the emulsion produced a well-adhering flexible and non-visible film.

Example 21: Preparation of a sunscreen cream "C"

1.33 g of light mineral oil was placed in a stainless steel ball grinder and 2 g of polymer were added and ground for 10 minutes. After reducing the speed, 1.617 g of a hydrophilic grease base is added and all components are mixed for 5 minutes, and 50mg of $TiO_2$ (aluminum hydroxide and stearic acid coated) is added and grinding at high speed is pursued 5 minutes to obtain the product.

Example 22: Preparation of a sunscreen cream "D"

1.33 g of light mineral oil was placed in the ball grinder and 2 g of polymer was added followed by 1.67 g of vaseline. The mixture is ground in a manner analogous to the preparation of the sunscreen cream "C"

Example 23: Preparation of a sunscreen cream "E"

1.33 g of light mineral oil was placed in the ball grinder and 2 g of polymer was added. A mixing technique identical to example 21 was used. Then, 1.665 g of vaseline was added and mixed for 5 minutes. 50 mg of $TiO_2$ (aluminum hydroxide and stearic acid coated) was added and the mixture milled for 5 minutes, to obtain a fine spreadable cream.

Example 24: Preparation of a sunscreen cream "G"

2.97 g of vaseline was placed into a stainless steel grinder, and 1.98 g of polymer was added, and the mixture ground for 10 minutes. 50 mg of $TiO_2$ (aluminum hydroxide and stearic acid coated) is added, and ground/mixed for 10 minutes to obtain the product.

Example 25: Polymerization of a UV A monomer and a UV B monomer with acrylic acid A 250 mL flask was charged with a 4-methacryloxydibenzoyl methane (1.2 g, $3.89 \times 10^{-2}$ mol), N-[2-(4'-dimethylamino benzoyl)oxy]propyl methacrylamide (14.65 g, $5.04 \times 10^{-2}$ mol), 140 mL toluene followed by acrylic acid (3.91 g, $5.43 \times 10^{-4}$ mol), and ethylene glycol dimethacrylate (0.19 g, $9.08 \times 10^{-4}$ mol). After achieving a homogenous solution with stirring, the vessel was flushed with nitrogen, and 2,2'-azobis isobutyronitrile (0.1 g, $6.09 \times 10^{-4}$ mol) was added to the flask. After stirring, (35–40 RPM) at 65° C. for 20 hours, the formed solid was filtered and washed with toluene. Resuspension with ethyl acetate at reflux for 30 hours and filtration afforded a pure powdery solid of particles, ranging from 0.7 to 3μ, which was vacuum dried to a mass of 17.34 g (86.5% yield).

In accordance with the invention, novel compositions are provided which give skin and eye protection from erythema, carcinogenicity and other deleterious effects of ultraviolet radiation, while biologically inert. The compositions have good retentive capability, provide a smooth coating on the skin, and do not unduly penetrate into the dermal layer, where the light absorbing moieties could have adverse effects. The compositions may be readily prepared from readily available compounds in accordance with conventional ways. For eye lenses, novel compositions are purified which are biologically and optically integral covalent parts of the lens to protect the eve from UV radiation, while the compositions are also biologically inert.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A dibenzoylmethane having an acryloxy or methacryloxy substituent at a para position.

2. Anisoate ester of acryloxyethanol, methacryloxyethanol, p-acrylamidophenol or p-methacrylamidophenol.

3. p-Dimethylaminobenzoate ester of 1-acrylamido- or 1-methacrylamido-2-propanol.

* * * * *